United States Patent [19]
Izawa et al.

[11] Patent Number: 5,820,625
[45] Date of Patent: Oct. 13, 1998

[54] LIGHT DEPILATING APPARATUS

[75] Inventors: Yoshihiro Izawa; Iwao Yamazaki, both of Tokyo, Japan

[73] Assignee: Ya-man Ltd., Tokyo, Japan

[21] Appl. No.: 755,569

[22] Filed: Nov. 27, 1996

[30] Foreign Application Priority Data

Sep. 26, 1996 [JP] Japan .................. 8-009690 U

[51] Int. Cl.$^6$ .................................. A61B 17/36
[52] U.S. Cl. .................. 606/9; 606/13; 607/88
[58] Field of Search ............... 606/3, 9–13; 607/88–89

[56] References Cited

U.S. PATENT DOCUMENTS

| | | | |
|---|---|---|---|
| 5,409,482 | 4/1995 | Diamantopoulos | 606/13 |
| 5,683,380 | 11/1997 | Eckhouse et al. | 606/9 |
| 5,683,436 | 11/1997 | Mendes et al. | 607/88 |

*Primary Examiner*—John P. Lacyk
*Assistant Examiner*—Roy Gibson
*Attorney, Agent, or Firm*—Kane, Dalsimer, Sullivan, Kurucz, Levy, Eisele and Richard, LLP

[57] ABSTRACT

A light depilating apparatus comprising a light depilating probe, an electric controller, and a connection cable for connecting the light depilating probe to the electric controller whereby the light depilating probe is brought into contact with a portion of skin to be depilated; wherein the light depilating probe includes: a hollow body; a head cap having opened and closed ends and being attached at its opened end to one end portion of the body so as to form an inner space in the head cap; a transparent contacting cylinder provided on a head of the head cap at its closed end so that the cylinder is brought into contact with skin; a holding block provided in the inner space of the head cap; a connection cap provided at the other end portion of the body to hold a terminal of the cable connected to the electric controller; a plurality of light-emitting sources constituted by semiconductor laser elements mounted in holes formed in the holding bock so as to be excited by the electric controller through electric conductors; holes provided in the closed end of the head cap so that light paths are formed though the holes of the holding block and the holes in the head cap respectively so as to make all the light beams emitted from the light-emitting sources are focused to one focal point within an outside end surface of the contacting cylinder which is brought into contact with skin.

9 Claims, 2 Drawing Sheets

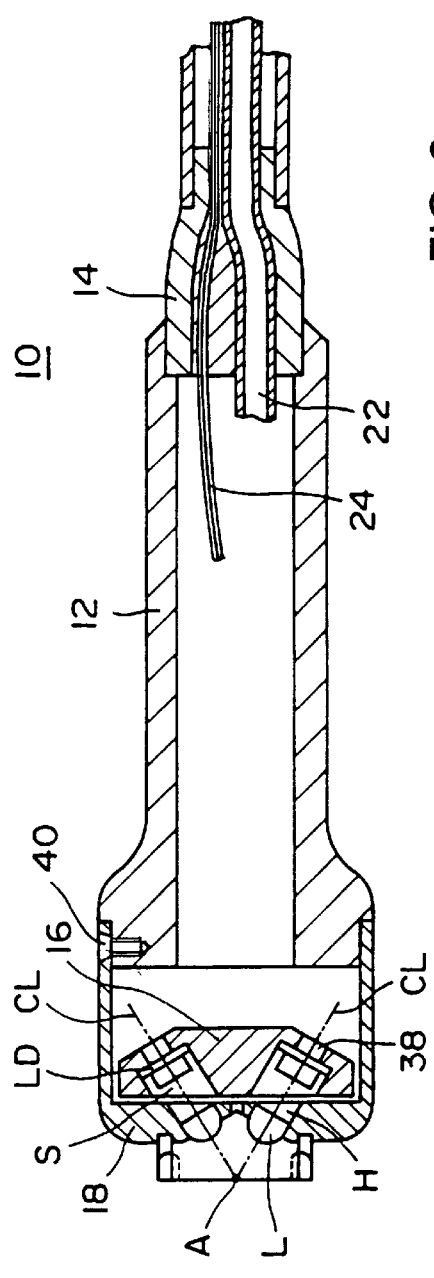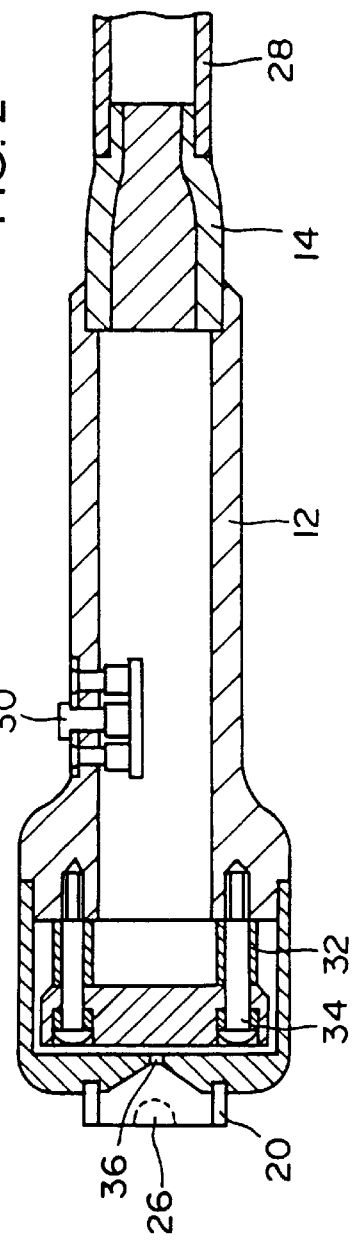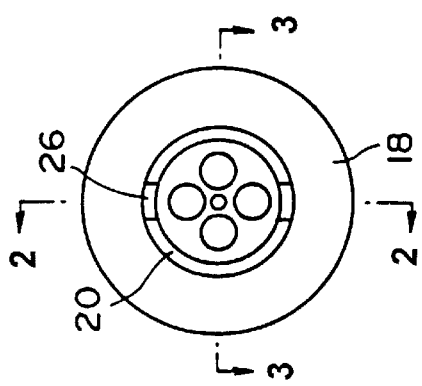

LIGHT DEPILATING APPARATUS

BACKGROUND OF THE INVENTION

1. Field of the Invention

The present invention relates to a light depilating apparatus, and particularly to a light depilating apparatus for performing permanent depilation by radiating laser light onto a desired portion of skin.

2. Description of the Prior Art

Various depilating apparatus for cosmetic treatment are known. In a high-frequency depilating apparatus which is disclosed in Japanese Utility Model Post-Examination Publication No. Hei-3-27620 (JP-U-3-27620), filed by the present applicant, high-frequency power is concentratively applied to the hair root portion of each of hairs to be depilated, so that the living organizations of the hair root portions are broken or depraved to attain permanent depilation. In this case, the hair root portion is picked up by a kind of pincette, and high-frequency power is concentratively applied thereto. Though depilating effects according to this method are desirable, the number of times of operations is large when hairs to be treated are many, and it takes long time to treat all the hairs. Therefore, it takes very much labor to distinguish hairs one by one and pick up each portion accurately, and it takes perseverance and patience after all.

In order to improve this point, the present applicant has proposed a light depilating apparatus in which treatment is hastened by radiating light having a spectral component of a visible light area onto the portion of wide area to be depilated (Japanese Patent Unexamined Publication No. Hei-3-66387 (JP-A-3-66387)). In this method, depilatory cream or wax is coated so that hairs to be depilated are depilated mechanically or chemically in advance. Next, for the sake of permanent depilation, the living organizations of hair root portions are broken by being photochemically dried or solidified so that the hairs cannot grow up again. However, this method has a difficult point that light is radiated also onto skin portions having no hairs, and light actually used for depilation is not more than a tenth of the whole of the radiated light so that the efficiency of use is smaller than that expected. In addition, the radiation area onto skin is so wide that a physical burden to the skin, such as a pain caused by heat rays, is conspicuous. Therefore, it has been proposed therein to use two kinds of light sources, a red one being for depilating, the other blue one being for appeasing pains.

In this regard, the present applicant has proposed, in Japanese Patent Unexamined Publication No. Hei-4-67860 (JP-A-4-67860), a light radiating probe for light depilation which can radiate light locally so as to concentrate the light in a hair root portion to be depilated. In this method, there are problems that a light-emitting source is a halogen lamp so that optics (that is, a combination of a lens system and an optical fiber system) for focusing and transmitting the light of the halogen lamp are considerably expensive, and in addition, only a part of a large amount of light emitted from the halogen lamp so that the efficiency is poor.

A laser source is known as a coherent light source which is superior in light focusing. A gas-oscillating laser light source, such as a carbon dioxide gas laser light source, can generate a large amount of light, and, in medical fields, it has been used, for example, for removing moles, birthmarks and blotches of skin. However, an apparatus using such a laser light source is expensive and, it is therefore not suitable for a small, simple and low-price apparatus for cosmetic treatment. With the recent advance of semiconductor technique, however, a laser light-emitting source has been developed which is easy to use, small in size and suitable particularly for cosmetic treatment.

SUMMARY OF THE INVENTION

It is therefore an object of the present invention to provide a light depilating apparatus which uses a semiconductor laser light source, which is comparatively small in physical burden, which can increase the effect of permanent depilation, which can be operated easily, which is small in size and light in weight, and which can be manufactured in low cost.

According to a first aspect of the present invention, the above object can be achieved by a light depilating apparatus comprising a light depilating probe, an electric controller for controlling the light depilating probe, and a connection cable for connecting the light depilating probe to the electric controller whereby the light depilating probe is brought into contact with a portion of skin to be depilated, wherein the light depilating probe includes: a hollow body; a head cap having an opened end and a closed end and being attached at its opened end to one end portion of the body so as to form an inner space in the head cap; a transparent contacting cylinder provided on a head of the head cap at its closed end so that the cylinder is brought into contact with skin; a holding block provided in the inner space of the head cap; a connection cap provided at the other end portion of the body so as to hold a terminal of the cable connected to the electric controller; a plurality of light-emitting sources constituted by semiconductor laser light-emitting elements mounted in holes formed in the holding bock so as to be excited by the electric controller through electric conductors; holes provided in the closed end of the head cap so that light paths are formed though the holes of the holding block and the holes in the head cap respectively so as to make all the light beams emitted from the light-emitting sources are focused to one focal point within an outside end surface of the contacting cylinder which is brought into contact with skin; and light-transmissive members respectively provided in the holes of the head cap for parting the inner space from the outside.

Further, according to a second aspect of the present invention, the above object can be achieved by a light depilating apparatus comprising a light depilating probe, an electric controller for controlling the light depilating probe, and a connection cable for connecting the light depilating probe to the electric controller whereby the light depilating probe is brought into contact with a portion of skin to be depilated; wherein the light depilating probe include: a hollow body; a head cap having an opened end and a closed end and being attached at its opened end to one end portion of the body so as to form an inner space in the head cap; a transparent contacting cylinder provided on a head of the head cap at its closed end so that the cylinder is brought into contact with skin; a holding block provided in the inner space of the head cap; a connection cap provided at the other end portion of the body so as to hold a terminal of the cable connected to the electric controller; a plurality of light-emitting sources including a plurality of semiconductor laser light-emitting elements and white lamps emitting light of a visible and infrared spectrum area, the semiconductor laser light-emitting elements and the white lamps being mounted in holes formed in the holding bock so as to be excited by the electric controller through electric conductors; holes provided in the closed end of the head cap so that light paths are formed though the holes of the holding block and the holes in the head cap respectively so as to make all the light beams emitted from the light-emitting sources are focused to one focal point within an outside end surface of the contacting cylinder which is brought into contact with skin and so as to make the light emitted from the white lamps is concentrated to the one focal point or its vicinity; and light-transmissive members respectively provided in the holes of the head cap for parting the inner space from the outside.

Other advantageous configurations of the light depilating apparatus according to the present invention are stated in the attached subclaims.

In the light radiating probe of the light depilating apparatus according to the present invention, a contact member is attached to the head of the probe to thereby keep a constant distance between the head of the probe and the portion of skin to be depilated. According to the first aspect of the present invention, a plurality of laser diodes are used as the light-emitting sources, and these laser diodes are installed in a holding block in the light radiating probe so that the light beams emitted from the laser diodes are focused substantially at one point on the portion of skin to be depilated.

On the other hand, according to the second aspect of the present invention, at least one white-light emitting source or white lamp is used in addition to the plurality of laser diodes. The white lamp emits light of a wide spectral range, that is, visible light and infrared light when an electric current is supplied to a tungsten wire sealed in the glass bulb of the lamp. These laser diodes and the white-light emitting source are installed in a holding block provided in the light radiating probe so that light beams emitted from the laser diodes and the white-light emitting source are focused substantially at one point on the portion of skin to be depilated.

Further, in order to prevent the deterioration of the laser diodes or the decrease of the efficiency caused by heat released from the laser diodes and the white-light emitting source themselves, and prevent the temperature rising of the light radiating probe itself, these laser diodes are buried in a support block made from material superior in thermal conductivity, such as aluminum or its alloy.

In addition, such a structure is employed that the support block for fixing the laser diodes and the white-light emitting source is exposed to the air supplied from the outside of the light radiating probe so as to be forced to be cooled. It is therefore possible to prevent the deterioration of the laser diodes and the decrease of the efficiency more effectively.

In this case, such a structure that the air used for cooling the laser diodes and the white-light emitting source forcedly can be made to concentratively hit the portion of skin to be irradiated with the laser light is employed. It is therefore possible to appease or release heat or pain caused by heat radiation of the laser light and the white light.

As for an external light-emitting-sources power supply to be connected to the light radiating probe, in the case of the first aspect, the plurality of the laser diodes are divided into a plurality of groups, preferably two groups, and a switching function is provided so that a light-emitting period and a pause period are alternately given to one group of the diodes while a reverse operation, that is, a pause period and a light-emitting period are alternately given to the other group of the diodes synchronously with each other. With such a pulse operating function, the laser diodes can be operated more effectively than they are made to oscillate continuously. Alternatively, such a method that a number of laser diodes are turned on for a constant period circulatingly and periodically is also effective.

In the second aspect, the plurality of laser diodes are divided into one or a plurality of groups, and a white-light-emitting lamp source is further provided as another group. The laser diodes are excited in the same manner as those in the first aspect, while various operation modes can be effected to the group of the white-light emitting source.

In a first operation mode, before radiation by the laser diodes, white light is radiated onto a desired portion of skin in advance so as to increase the metabolism of living organizations of the skin to make the depilating effect by the radiation of the laser diodes more effective.

In a second operation mode, white light is radiated onto the same radiation position and at the same time as the radiation by the laser diodes. By this operation, the depilating effect itself is made more effective.

In a third operation mode, after radiation by the laser diodes, white light is radiated with slightly weak intensity onto the irradiated portion. By this operation, the physical burden, particularly the pain of the skin, caused by the depilating treatment is released or suppressed.

A processing program for an electric controller used in the present invention is selected properly so that one of the above-mentioned operation modes, or a desired combination thereof is performed. Thus, it is possible to make the depilating effect by the laser light radiation more effective.

In the light depilating apparatus according to the present invention, it is dangerous to apply intensive laser beams to skin or a body for a long time. Accordingly, a protection circuit should be provided in the control circuit so as to limit the current conduction period in accordance with the intensity of the emitted beams.

As known well, the cost of a laser diode is very high not in proportion to its output value. Being constituted by a combination of a plurality of laser diodes the output values of which are comparatively low, the light radiating probe according to the present invention is advantageous from the point of economical view.

BRIEF DESCRIPTION OF THE DRAWINGS

FIG. 1 is a front view of a light radiating probe of a light depilating apparatus according to the present invention as viewed from a head portion;

FIG. 2 is a longitudinal sectional view of the light radiating probe illustrated in FIG. 1 taken in the direction of arrows 2—2;

FIG. 3 is a longitudinal sectional view of the light radiating probe illustrated in FIG. 1 taken in the direction of arrows 3—3.

DETAILED DESCRIPTION OF THE PREFERRED EMBODIMENT

Figure 4:
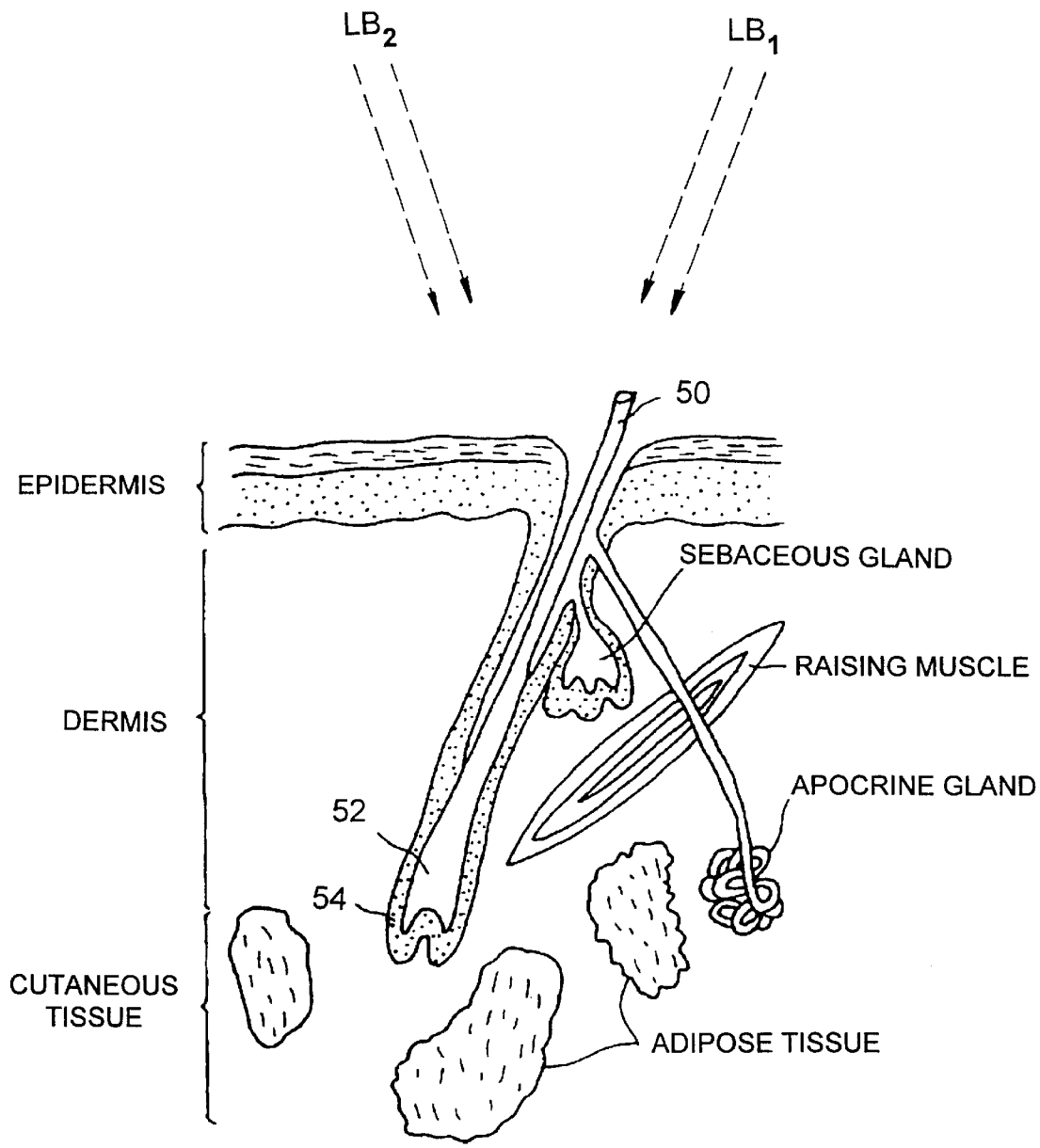
FIG. 4 is a schematic sectional view illustrating a real hair root and the directions of light beams radiated thereto.

An embodiment of the first aspect of the present invention will be described in detail with reference to the drawings to explain the light depilating apparatus according to the present invention.

FIG. 1 shows a light radiating probe 10 of a light depilating apparatus according to the present invention. In FIG. 1 is a front view viewed from the head portion. FIG. 2 is a longitudinal sectional view viewed in the direction of arrows 2—2. FIG. 3 and is a longitudinal sectional view viewed in the direction of arrows 3—3. A body 12 of the light radiating probe 10 is a hollow cylinder made from synthetic resin such as ABS resin. This body 12 is made somewhat larger in its outer diameter and thicker in its thickness as its left end. A hollow head cap 18 similarly made from synthetic resin is attached to the left end of the body 12 and fixed thereto by means of a screw 40 so as to form a space for receiving laser diodes LD therein. A hollow contact cylinder 20 having an outer diameter smaller than that of the head cap 18 is fixedly attached to the head cap 18. This contact cylinder 20 is made from transparent synthetic resin such as transparent acrylate resin so that it is convenient for an operator to select or decide the portion of skin to be irradiated while observing from the outside. A connection cap 14 made of, for example, hard rubber is inserted into the right end of the body 12 so as to seal it. Further, a cable 28 of conductors 24 and a conduit 22 is connected to the right end of the connection cap 14.

The head cap 18 has four holes H as shown in FIG. 1. The head cap 18 further has a thin center hole 36 which is formed at its diametrical center so as to penetrate the head cap 18 to exhaust air. In each of the holes H of the head cap 18, a hemispherical beam-focusing lens L made from transparent synthetic resin is sealed air-tightly. A block 16 formed of aluminum or its alloy for holding light-emitting sources is received in the inner space of the head cap 18. In this case, this block 16 is fixed at four places by means of screws 34 which are screwed down through sleeves 32 into four tapped holes provided in the end surface of the body 12 respectively (FIG. 3). Four holes S are provided also in the light-emitting source holding block 16 so that four laser diodes LD each made from an AlGaAs semiconductor are installed in the four holes S' respectively. The holes S of the holding block 16 and the holes H of the head cap 18 are aligned on one and the same axes CL respectively. In this case, each of the axes (that is, optical axes of the laser diodes) CL is different from the direction of the axis of the head cap 18 or the body 12. That is, the axis CL is disposed obliquely relative to this longitudinal axis of the body 12 so as to be directed to the diametrical center of the leftmost end of the contact cylinder 20, that is, a diametrical center A (FIG. 2) in the contact surface area of skin to be depilated.

As for the shape of the holding block 16, other than the illustrated shape, it is effective to additionally provide roughness, webs, grooves or the like in the surface of the holding block 16 in order to improve the efficiency in releasing heat.

Though whole wiring is not shown in the drawing in order to simplify the drawing, the conductors 24 introduced through the cable 28 from a not-shown electric controller are connected to the semiconductor diodes LD through the connection cap 14, the body 12 and the holes 38 of the holding block 16, and are connected also to a switch 30 attached to the body 12 for starting and stopping the radiation of the radiating probe 10. A switching signal from this switch 30 is introduced to a power supply circuit of the not-shown electric controller. The air conduit 22 is also introduced into the inner space of the body 12 through the cable 28 and the connection cap 14 from a compressed air generating portion of the not-shown electric controller. The introduced air blows out toward the radiation position A, which has been described above, from the center hole 36 of the head cap 18 through a gap between the inner wall of the head cap 18 and the outer surface of the holding block 16. This air is released to the outside through two notches 26 formed in the contact cylinder 20.

The semiconductor laser diodes LD used in the light radiating probe 10 according to the present invention are of AlGaAs which emits near-infrared light the wavelength of which is 785 mm particularly effective to dry or solidify living organizations of hair root portions photochemically. Four light radiation beams different in the traveling direction from each other are generated in the light depilating apparatus according to the present invention (only two beams are shown in FIG. 4). That is, light beams $LB_1$ and $LB_2$ are generated so as to travel obliquely relative to the vertical direction to skin. As known well, a hair 50 generally grows obliquely relative to the vertical direction to skin. To make near-infrared light reach a living organization 54 of a hair root portion 52 of such a hair, when the light is radiated in the direction of this hair, the radiated light enters a deep portion along the hair, effectively to photochemically transform a subcutaneous tissue near the hair root. It should be therefore noted that more effective depilation can be performed in the light depilating apparatus according to the present invention than in an apparatus using radiation of only vertical incident light beams.

In an embodiment of the apparatus according to the second aspect of the present invention, the shape of the holding block 16 is substantially the same as that in the apparatus according to the first aspect of the present embodiment. It is however necessary to change the support portion for the laser diodes LD so that white lamps can be mounted. However, there is no change in the holes H provided in the head cap 18 and no change in the sealing members attached to the top end of these holes H for the sake of sealing. Because the head portion of a bulb of the white lamp is shaped like a lens, generally, it is not necessary to make the sealing members have a beam-focusing lens function. Therefore, it is sufficient that the sealing members constituted by simple transparent flat plates of plastics.

When depilating treatment is performed by means of the light depilating apparatus according to the present invention, first, portions of hairs to be depilated projecting over the skin surface are shaved or eliminated with depilatory cream or the like in advance. After that, the contact cylinder 20 of the light depilating probe 10 is brought into contact with the skin tightly so that the hair 50 left in the skin surface is substantially coincident with the focal point A as shown in FIG. 4. Next, the switch 30 is turned on to perform light radiation with light radiation intensity and in a radiation period in accordance with a treatment mode set in an electric controller attached thereto. If hairs to be depilated are left in the circumference, the same operation is given to the hairs. Last, the contact cylinder 20 is detached from the skin, suitable cosmetic cream or cosmetic liquid is applied to appease the inflammation of the skin, and massage is given thereto if necessary.

The light depilating apparatus according to the present invention described above may be modified or changed variously. The present invention is not limited to the illustrated figures. For example, the number of the laser diodes is not limited to four, but the apparatus may be configured so as to have two or more laser diodes. In addition, it is not always necessary to make the beam-focusing lens L hemispherical. It may be a glass plate or a plastic plate which is simple and flat. Although the through hole 36 of the head cap 18 was illustrated as only one center hole at the position corresponding to the longitudinal axis of the probe 10, the number is not limited to one. A plurality of holes may be provided in desired positions of the head cap 18, and the air to be exhausted near the focal point A may be blown. Any light depilating apparatus having a structure set forth in the scope of the claims of the present invention belongs to the scope of the present invention.

What is claimed is:

1. A light depilating apparatus comprising a light depilating probe, an electric controller for controlling said light depilating probe, and a connection cable for connecting said light depilating probe to said electric controller whereby said light depilating probe is adapted to be brought into contact with a portion of skin to be depilated;

wherein said light depilating probe includes:
a hollow body;
a head cap having an opened end and a closed end and being attached at its opened end to one end portion of said body so as to form an inner space in said head cap;
a transparent contacting cylinder provided on a head of said head cap at its closed end so that said cylinder is adapted to be brought into contact with skin;
a holding block provided in the inner space of said head cap;
a connection cap provided at the other end portion of said body so as to hold a terminal of said cable connected to said electric controller;
a plurality of light-emitting sources constituted by semiconductor laser light-emitting elements mounted in holes formed in said holding block so as to be excited by said electric controller through said connection cable;
holes provided in said closed end of said head cap so that light paths are formed through said holes of said holding block and said holes in said head cap respectively so as to make all the light beams emitted from said light-emitting sources focus to one focal point within an outside end surface of said contacting cylinder which is brought into contact with skin; and
light-transmissive members respectively provided in said holes of said head cap for separating said inner space from the outside.

2. A light depilating apparatus according to claim 1, wherein:
said light-transmissive members provided in said holes of said head cap of said light depilating probe are formed of synthetic resin or glass and comprise hemispherical members having a beam focusing lens function, or convex members having a beam-focusing lens function, or flat members having no beam-focusing lens function.

3. A light depilating apparatus according to claim 2, wherein:
said holding block for holding said light-emitting sources is formed of material light in weight and superior in thermal conductivity, and part of or all of a surface of said holding block is held in said body without contacting with the inner wall of said head cap;
at least one through hole is provided in said closed end side of said head cap so as to be directed to the vicinity of said focal point;
compressed air from a compressed-air generator provided in said electric controller is introduced into a hollow space of said body through an air conduit of said cable, and said air is moved along the surface of said holding block and released through said at least one through hole; and
at least one air exhaust hole is provided in a circumferential side surface of said contacting cylinder.

4. A light depilating apparatus according to claim 3, wherein:
said electric controller is configured so that said semiconductor laser light-emitting elements are classified into a plurality of groups, and the semiconductor laser light-emitting elements of each of said groups repeats oscillation and pause alternately so that when one of said groups oscillates, the other groups make a pause.

5. A light depilating apparatus comprising a light depilating probe, an electric controller for controlling said light depilating probe, and a connection cable for connecting said light depilating probe to said electric controller whereby said light depilating probe is adapted to be brought into contact with a portion of skin to be depilated;

wherein said light depilating probe includes:
a hollow body;
a head cap having an opened end and a closed end and being attached at its opened end to one end portion of said body so as to form an inner space in said head cap;
a transparent contacting cylinder provided on a head of said head cap at its closed end so that said cylinder is adapted to be brought into contact with skin;
a holding block provided in the inner space of said head cap;
a connection cap provided at the other end portion of said body so as to hold a terminal of said cable connected to said electric controller;
a plurality of light-emitting sources including a plurality of semiconductor laser light-emitting elements and white lamps emitting light of a visible and infrared spectrum area, said semiconductor laser light-emitting elements and said white lamps being mounted in holes formed in said holding block so as to be excited by said electric controller through said connection cable;
holes provided in said closed end of said head cap so that light paths are formed through said holes of said holding block and said holes in said head cap respectively so as to make all the light beams emitted from said light-emitting sources focus to one focal point within an outside end surface of said contacting cylinder which is brought into contact with skin and so as to make the light emitted from said white lamps concentrated to said one focal point or its vicinity; and
light transmissive members respectively provided in said holes of said head cap for separating said inner space from the outside.

6. A light depilating apparatus according to claim 5, wherein:
said light-transmissive members provided in said holes of said head cap of said light depilating probe are formed from synthetic resin or glass and comprise one of hemispherical members having a beam-focusing lens function, or convex members having a beam-focusing lens function, or flat members having no beam-focusing lens function.

7. A light depilating apparatus according to claim 6, wherein:
said holding block for holding said light-emitting sources is formed of material light in weight and superior in thermal conductivity, and part of or all of a surface of said holding block is held in said body without contacting with the inner wall of said head cap;
at least one through hole is provided in said closed end side of said head cap so as to be directed to the vicinity of said focal point;
compressed air from a compressed-air generator provided in said electric controller is introduced into a hollow space of said body through an air conduit of said cable, and said air is moved along the surface of said holding block and released through said at least one through hole; and at least one air exhaust hole is provided in a circumferential side surface of said contacting cylinder.

8. A light depilating apparatus according to claim 7, wherein:

said electric controller is configured so that said light-emitting sources are classified into at least one group of said white lamps and a plurality of groups of said semiconductor laser light-emitting elements, and when one group of said semiconductor laser light-emitting elements oscillate, the other groups of said semiconductor laser light-emitting elements make a pause, and said group of said white lamps can be excited to radiate white light before, and/or while, and/or after light beams of said semiconductor laser light-emitting elements are radiated.

9. A light depilating apparatus according to any of claims 4 to 8, wherein:

a switch for designating start of operation of said light depilating apparatus is provided in said body; and said electric controller includes a timer circuit for interrupting the excitation of said semiconductor laser light-emitting elements after predetermined time in accordance with light-emitting outputs of said semiconductor laser light-emitting elements.

* * * * *